United States Patent [19]

Giaever

[11] 3,979,509
[45] Sept. 7, 1976

[54] OPAQUE LAYER METHOD FOR DETECTING BIOLOGICAL PARTICLES

[75] Inventor: Ivar Giaever, Schenectady, N.Y.

[73] Assignee: General Electric Company, Schenectady, N.Y.

[22] Filed: Sept. 3, 1974

[21] Appl. No.: 503,030

[52] U.S. Cl. .............................. 424/12; 23/230 B; 23/253 TP; 195/103.5 R
[51] Int. Cl.$^2$ .................. G01N 33/16; G01N 21/04
[58] Field of Search ........ 23/230 B, 253 R, 253 TP, 23/424; 424/12; 195/103.5 R

[56] References Cited
UNITED STATES PATENTS
3,853,467   12/1974   Giaever.............................. 23/253 R Primary Examiner—Morris O. Wolk
Assistant Examiner—Sidney Marantz
Attorney, Agent, or Firm—Leo I. MaLossi; Joseph T. Cohen; Jerome C. Squillaro

[57] ABSTRACT

A monomolecular layer of first biological particles is adsorbed on the surface of a substrate fabricated of virtually any nonreactive solid material, the coated substrate is then exposed to a solution suspected of containing second biological particles specific to the first biological particles, next a porous, opaque layer of nonreactive third particles is formed in the coated substrate, and then the coated substrate is exposed to a cleaving agent solution which cleaves the bond between the first and second biological particles. A visual examination of the coated substrate surface clearly indicates to the naked eye or examination by suitable instrument whether the suspect solution contains the second biological particles by determining whether the opaque layer is complete or a portion common to the second biological particles, has been removed.

29 Claims, 2 Drawing Figures

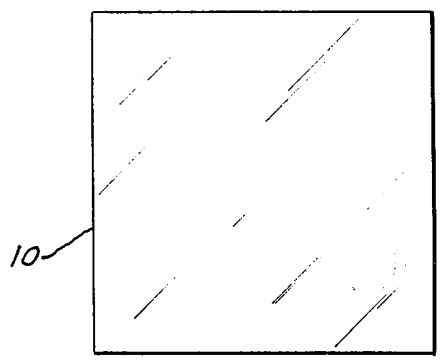
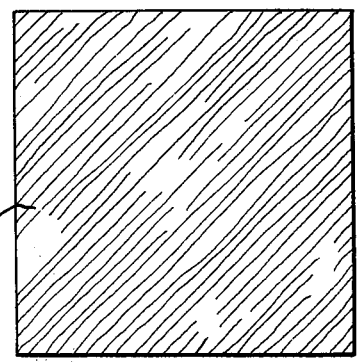
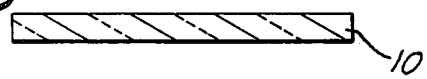
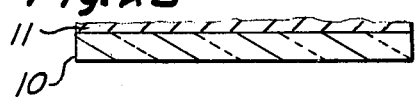
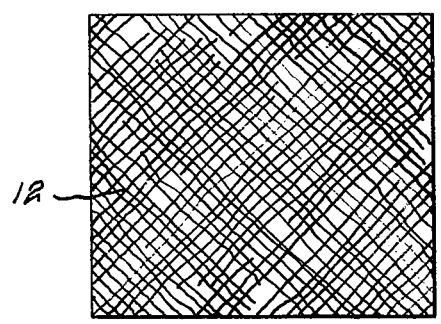
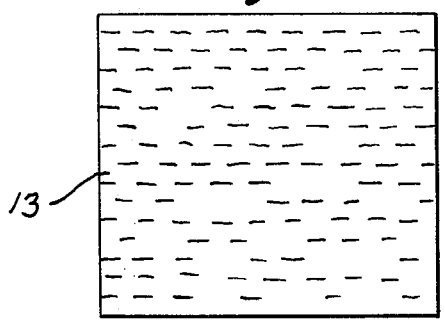
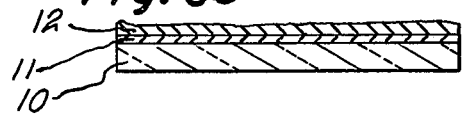
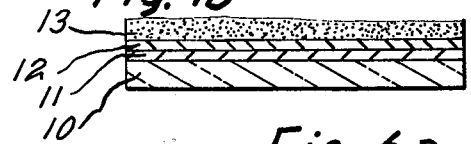
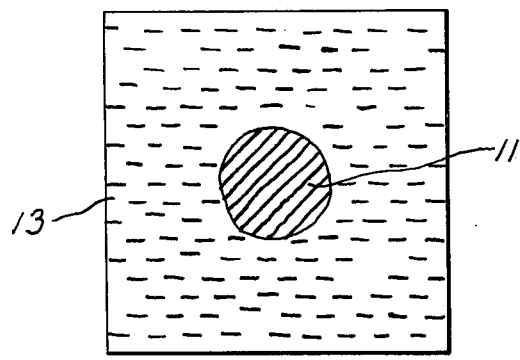
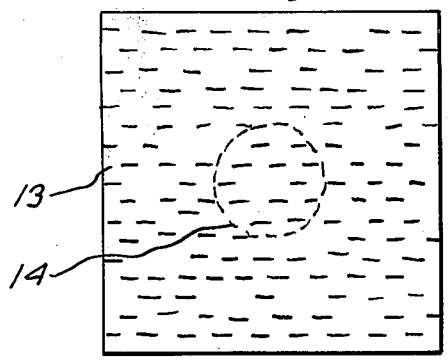
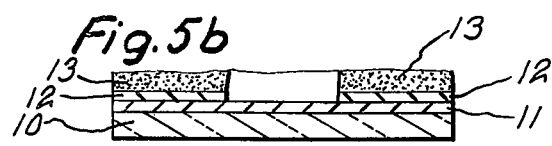
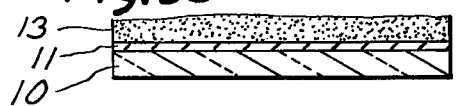

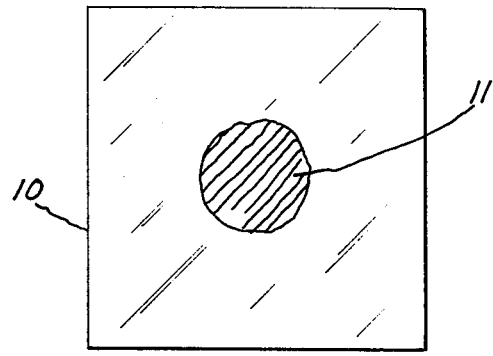
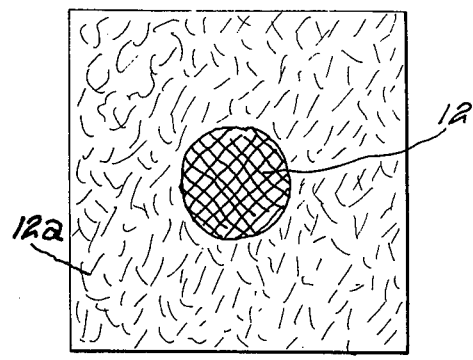
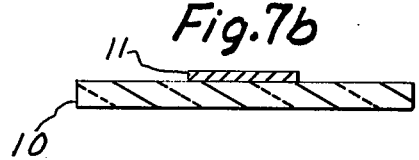
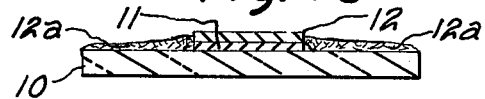
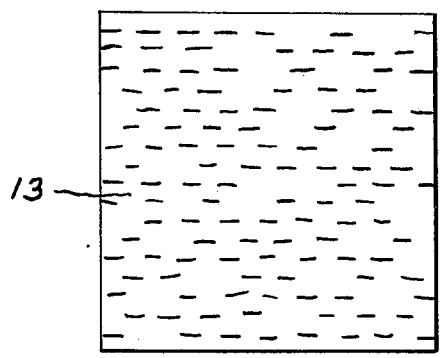
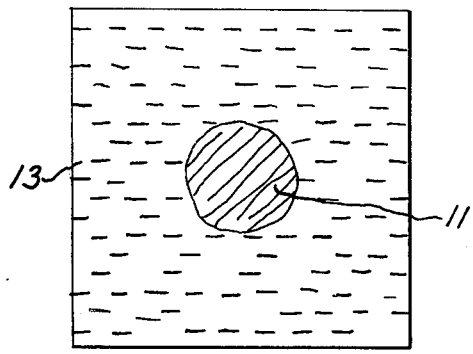
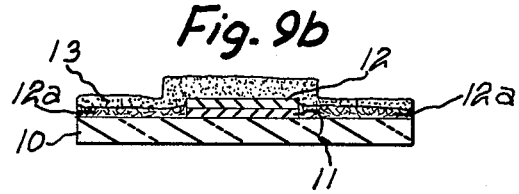
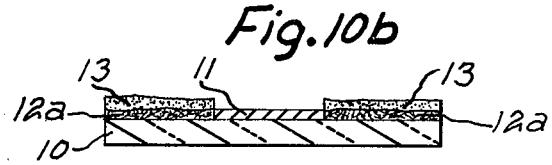

OPAQUE LAYER METHOD FOR DETECTING BIOLOGICAL PARTICLES

My invention relates to a medical diagnostic method and apparatus for detecting an immunologic (as well as other specific) reactions occurring on the surface of a substrate fabricated of virtually any nonreactive solid material, and in particular, to the method and apparatus utilizing the substrate with an opaque layer of nonreactive particles that provides good contrast to the unaided eye or suitable instrument for indicating the occurrence of the immunologic reaction.

This application is related to my copending patent applications Ser. No. 266,278 entitled "Method and Apparatus for Detection and Purification of Proteins and Antibodies" filed June 26, 1972, abandoned; Ser. No. 384,113 entitled "Improved Method and Apparatus for Detection and Purification of Proteins and Antibodies" filed July 30, 1973, abandoned, and Ser. No. 445,204 entitled "Improved Substrate for Immunological Tests and Method of Fabrication Thereof" filed Feb. 25, 1974 U.S. Pat. No. 3,926,564, and assigned as herein. Other publications related to the present invention primarily as background are "Optical Measurement of the Thickness of a Film Adsorbed from a Solution", authors Irving Langmuir et al, Journal of the American Chemical Society, Vol. 59 (July–December 1937) pg. 1406; "Immunologic and Enzymatic Reactions Carried Out at a Solid-Liquid Interface" by Alexandre Rothen, Physiological Chemistry and Physics, 5, (1973), pgs. 243–258, "Interactions Among Human Blood Proteins at Interfaces", Leo Vroman et al, Federation Proceedings, Vol. 30, No. 5 (Sept.–Oct. 1971) pgs. 1494–1502, "The Antibody-Antigen Reaction: A Visual Observation", Ivar Giaever, The Journal of Immunology, Vol. 110, No. 4 (May 1973) pgs. 1424–1426, and "Three Simple Ways to Detect Antibody-Antigen Complex on Flat Surfaces", A. L. Adams et al, Journal of Immunological Methods 3 (1973) pgs. 227–232.

Immunological reactions are highly specific biophysical reactions in which a first immunologically reactive biological particle (generally a protein) known as the antigen combines (links) with a second protein specific to the antigen, and known as the antibody, to form an immunologically complexed protein. Immunological reactions taking place within a biological system such as an animal or human being are vital in combatting disease. In a biological system, the entry of a foreign protein, i.e., the antigen, causes the biological system to produce the specific antibody proteins to the antigen in a process not fully understood at this time. However, some of the most important antibodies used in diagnostic reactions are not related to the entry of any known foreign molecule. Some antibodies, such as anti-A and anti-B used in blood grouping, are called natural antibodies, because they are found in human sera apparently without the requirement of prior antigenic stimulation. Other antibodies seem to have the ability to react with some constituents normally present in the body. This leads to the pathological condition known as autoimmunity or autoallergy. Examples of such antibodies include the antinuclear antibodies of systemic lupus erythmatosus, the rheumatoid factors of rheumatoid arthritis, and the anti-thyroglobulin antibodies of chronic thyroiditis (Hashimoto's Disease). The antibody protein molecules have available combining or binding sites which complement those of the antigen molecule so that the antigen and antibody link or bond to form an immunologically complexed protein.

Most antigens are proteins or contain proteins as an essential part, whereas all antibodies are proteins. Proteins are large molecules of high molecular weight, i.e., are polymers consisting of chains of variable numbers of amino acids. The above-cited copending applications disclose that an arbitrary protein will adhere to a substrate in a monomolecular layer only, and that no other arbitrary protein will adhere to the protein layer. On the other hand, the specifically reacting protein to the first protein adsorbed onto the substrate will immunologically bond thereto. In accordance with the teachings of those applications, this discovery is exploited to provide medical diagnostic apparatus in which a particularly prepared slide having a monomolecular layer of one protein adsorbed thereon is used to test suspected solutions for the presence of the specifically reacting protein thereto. If the specifically reacting protein is present in the solution, the slide after exposure to the solution has a bimolecular protein layer thereon. If the specifically reacting protein is absent from the solution, the slide after exposure to the solution has only the original monomolecular protein thereon. Optical, electrical and chemical means for distinguishing between bimolecular and monomolecular biological particle layers are taught in the related copending applications and have different degrees of sensitivity and economy. Examination of the protein coated slide with the unaided eye would be the preferred approach for determining the number of biological particle layers on the slide due to its simplicity and the above-identified copending patent application teach such approach.

The detection of antibodies in a biological system is of medical diagnostic value in determining the antigens to which the system has been exposed. An example of diagnostic detection of antibodies is the detection of antibodies to syphilis or gonorrhea in human serum. Conversely, the detection of certain antigens in a biological system also has medical diagnostic value; examples of diagnostic detection of antigens include detection of HCG-protein molecules in urine as a test for pregnancy, and detection of hepatitis-associated-antigen (HAA) molecules in the blood of prospective blood donors.

In order to perform such diagnostic tests, the appropriate protein of the immunologically reacting pair must be obtained. At present, the source of an antibody protein must be a living biological system. More particularly, vertebrates are known to exhibit immunological reactions to the introduction of a foreign protein. For example, many antibodies are found in the blood serum of animals and human being which have been exposed to the corresponding antigens. Invertebrates also exhibit immunological reactions, although they probably do not have specific memory. Even some plant proteins combine with antigens and these so-called lectins may be of considerable use in diagnostic reactions. Some antigens may be controllably produced in laboratory cultures. However, most antigens, for example, hepatitis-associated-antigens, are at present like antibodies, only obtainable from living biological systems and thus many antigens are obtained from natural sources such as human or animal tissues.

It is known in the immunological art that antibody molecules function as antigens when introduced into the system of a vertebrate to whom they are foreign proteins. Accordingly, specifically reacting antibodies to a given antibody may be produced in such vertebrate system.

Although the emphasis herein will be on biological particles that immunologically react with each other, my invention also includes other forms of biological interactions between large molecules based on nonimmunological specifications such as for example, the binding of enzymes to their biological substrates, or hemoglobin to haptoglobin.

Although the substrates (slides) described in the hereinabove referenced patent applications are satisfactory in their performance, they generally must be specifically prepared, that is, a slide formed of glass or plastic is coated with a metal in order to enhance the contrast between single and double monomolecular layers and thus added cost and complexity of the medical diagnostic apparatus is inherent.

Therefore, a principal object of my invention is to provide an improved method and apparatus for detecting immunological and other forms of biological reactions occurring at a solid surface by direct visual observation, or by instrumentation.

Another object of my invention is to provide a method and apparatus wherein any substrate that is nonreactive with the biological reaction can be utilized.

A further object of my invention is to provide a method and apparatus wherein the detection of a biological reaction is obtained by a cleavage of the bond between the biological particles along a portion of the substrate surface.

Briefly, and in accordance with the objects of my invention, I provide a method and apparatus for detecting particular biological particles by examining with the unaided eye the coated surface of a substrate formed of a wide variety of materials nonreactive with the biological particles so as to detect a biological reaction occurring at the solid surface thereof. This wise choice of substrate materials is an important aspect of my invention. A monolayer of first biological particles is initially adsorbed along a portion of the surface of the substrate and the coated substrate is then immersed in, or otherwise exposed to, a solution suspected of containing second biological particles that are specific to the first particles. After the substrate has been exposed to the suspect solution for a sufficient length of time for the second particles, if present, to form a monomolecular layer thereof, the substrate is removed from the solution and an opaque, porous layer of third particles nonreactive with the substrate and first and second biological particles is formed as a complete outermost layer on the substrate. The coated substrate member is subsequently exposed to a weak acid solution or other cleaving agent for cleaving the bond that exists between the first and second biological particles, assuming the suspect solution did contain such second biological particles. The cleavage of the bond is clearly visible to the unaided eye (or by instrumentation) due to the significant contrast between the opaque layer and the portion thereof removed as the result of the cleavage, thereby indicating the presence of the second biological particles in the suspect solution. Absence of the second biological particles in the suspect solution results in the opaque layer remaining complete.

The features of my invention which I desire to protect herein are pointed out with particularity in the appended claims. The invention itself, however, both as to its organization and method of operation together with further objects and advantages thereof, may best be understood by reference to the following description taken in connection with the accompanying drawings wherein:

FIG. 1a is a plan view of a substrate used in my apparatus for detecting biological particles;

FIG. 1b is an elevation view in section through the center of the substrate depicted in FIG. 1a;

FIG. 2a is a plan view of the substrate after a monomolecular layer of first biological particles have been adsorbed on the entire top surface thereof;

FIG. 2b is an elevation view in section through the center of the substrate and first monomolecular layer depicted in FIG. 2a;

FIG. 3a is a plan view of the monomolecular layer coated substrate after it has been exposed to a solution containing second biological particles that are specific to the first particles to thereby form a second monomolecular layer along the entire top surface of the substrate;

FIG. 3b is an elevation view in section through the center of the substrate and two monomolecular layers depicted in FIG. 3a;

FIG. 4a is a plan view of the coated substrate of FIG. 3a after a nonreactive, opaque, porous third layer has been formed along the outer surface of the second monomolecular layer;

FIG. 4b is an elevation view in section through the center of the three layer coated substrate depicted in FIG. 4a;

FIG. 5a is a plan view of the coated substrate depicted in FIG. 4a after a portion of the coated substrate has been exposed to a weak acid solution that cleaves the bond between the first and second biological particles in a first embodiment of my invention;

FIG. 5b is an elevation view in section through the center of the apparatus depicted in FIG. 5a;

FIG. 6a is a plan view of the nonreactive opaque, porous layer coated substrate in the absence of the monolayer of second biological particles and after it has been exposed to the weak acid solution;

FIG. 6b is an elevation view in section through the center of the apparatus depicted in FIG. 6a;

FIG. 7a is a plan view of the substrate in a second and preferred embodiment of my invention wherein the monolayer of first biological particles is adsorbed along only a portion of the substrate surface;

FIG. 7b is an elevation view in section through the center of the apparatus depicted in FIG. 7a;

FIG. 8a is a plan view of the monolayer coated substrate of FIG. 7a after it has been exposed to the second biological particle solution to form the second monolayer;

FIG. 8b is an elevation view in section through the center of the apparatus depicted in FIG. 8a;

FIG. 9a is a plan view of the coated substrate of FIG. 8a after the nonreactive, opaque, porous third layer has been formed over the entire surface of the substrate;

FIG. 9b is an elevation view in section through the center of the apparatus depicted in FIG. 9a;

FIG. 10a is a plan view of the coated substrate of FIG. 9a after it has been exposed to the weak acid solution in the preferred embodiment of my invention;

FIG. 10b is an elevation view in section through the center of the apparatus depicted in FIG. 10a;

FIG. 11b is an elevation view in section through the center of the apparatus depicted in FIG. 11a;

FIG. 12b is an elevation view in section through the center of the apparatus depicted in FIG. 12a;

FIG. 13b is an elevation view in section through the center of the apparatus depicted in FIG. 13a;

FIG. 14b is an elevation view in section through the center of the apparatus depicted in FIG. 14a.

Figure 11A:
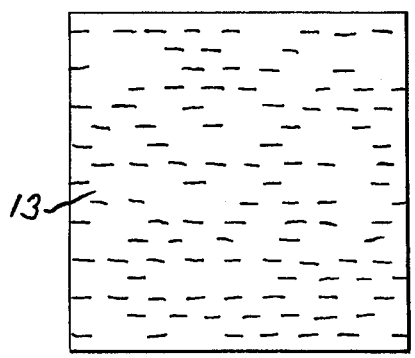
FIG. 11a is a plan view of the coated substrate of FIG. 10a in the absence of the monolayer of second biological particles and after exposure to the weak acid solution.
Figure 12A:
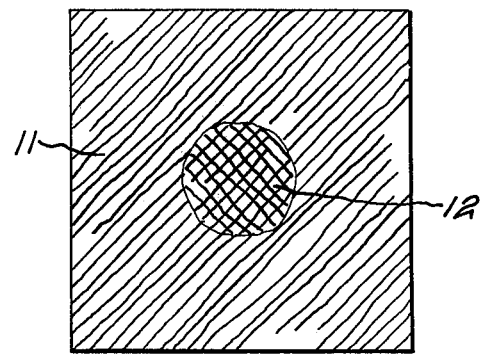
FIG. 12a is a plan view of the substrate after it has been exposed to the second biological particle solution to form the second monolayer in a third embodiment of my invention.

Referring now to FIGS. 1a and 1b, there are shown a plan and elevation view, respectively, of a typical substrate member 10 that may be utilized in my method and apparatus for detecting an immunologic or other specific reaction and therefore, specific biological particles. A major advantage of my present invention over that disclosed in my copending application Ser. No. 445,204 is that substrate member 10, herein foreshortened to the word "substrate" for convenience, may be fabricated of virtually any solid material that is nonreactive with the biological particles utilized with the substrate and an opaque third layer to be described hereinafter. The surface of substrate 10 must be impermeable and non-absorbant to the solutions of biological particles and opaque layer material and must permit the adsorption of a monomolecular layer of the first biological particles thereon. Thus, substrate 10 may be fabricated of any suitable material such as glass, plastic or a metal, with glass or plastic having economic advantages. The shape and thickness of substrate 10 are also immaterial, and for convenience a square shaped substrate of thickness in the order of one-fourth millimeter may typically be utilized. Although it is preferable that the top surface of substrate 10 be substantially flat, this is not a limitation and such surface can be slightly nonplanar. As a typical example, substrate 10 may be in the form of a glass slide such as a conventional microscope cover glass 25 millimeters (mm) square and ¼ mm thick, the glass slide being a convenient embodiment due to its low cost and ready commercial availability. The size of substrate 10 is governed primarily by the particular medical diagnostic application to be utilized. Thus, in the case of only a single test, substrate 10 is sufficiently small, in the order of the 25 millimeter square described hereinabove, whereas for an application wherein a plurality of specimens are to be analyzed simultaneously, or successively, the size of substrate 10 is sufficiently larger to accompany the plurality of samples to be tested. The only requirements of substrate 10 are that it present a solid surface to the biological particles involved in the particular diagnostic test, the solid surface be relatively free of defects so that it will be reasonably smooth although it need not be perfectly planar, and finally that it not be reactive with the biological particles or the material in the opaque layer. No special preparation of the substrate surface is required, that is, for example, a microscope glass slide used as the substrate may be utilized in its pre-cleaned condition upon removal from its place of storage. If a separate cleaning process for the substrate is used, the substrate must be thoroughly rinsed to assure that undesired deposits from the cleaning material, which might prevent or impede adsorption of the first monolayer of biological particles thereon, do not remain on the substrate surface.

Upon selection of substrate 10, a monomolecular layer 11 of a first immunotogically reactive biological particle is adsorbed along the top solid surface of substrate 10. The emphasis herein will be on immunologically reactive biological particles (the simplest case being the antigen-antibody pair), for purposes of simplicity; however, it should be understood that my invention is equally useful with biological particles that undergo forms of biological interaction other than the immunologic reaction, the only criteria being that the particles are specific to each other. The adherence of the first biological particles may be accomplished by depositing one or more drops of a first solution of the first biological particles on the substrate top surface by utilizing a suitable dropper or other means. Alternatively, substrate 10 may be dipped momentarily into the solution of the first biological particles. The first biological particles are selected on the basis of being specific to particular second biological particles which will form the second layer on the substrate surface if they are present in a second solution, or sample thereof, to be tested. The first biological particles may be produced in laboratory cultures or obtained from the higher living biological systems as described hereinabove, and are generally commercially available in a relatively highly purified form, and if not available commercially, may be purified chemically. The solution of the first biological particles may be a salt solution of water or other liquid approprate to, and not reactive with the first biological particles and the substrate material. A more detailed description of the formation of the first (and second) particle monolayers in all the embodiments of my present invention is included in the teachings of the aforementioned copending U.S. patent applications of Giaever which are herein incorporated by reference. The time interval (generally up to one hour) for the formation of the first monomolecular layer 11 on substrate 10 is an inverse function of the concentration of the first biological particles in the first solution. The first monomolecular layer 11 covers substantially the entire top surface of substrate 10 in this first embodiment of my invention as depicted in FIGS. 2a and 2b. Substrate 10 is therefore made as small as practical in order to conserve the amount of biological material used in the process. A rinsing of the monomolecular layer coated surface of substrate 10 with tap water or distilled water is recommended in order to remove excess first biological particles (and possibly others existing in the first solution) that may accumulate on top of the monolayer. The monolayer coated substrate is then dried, if the substrate is to be shipped commercially or stored, preferably by blowing air at room temperature across the substrate in order to speed the drying process. If the substrate is to be used immediately, there is no need to dry it after the rinsing. The first monomolecular layer 11 is generally invisible to the unaided eye since the thickness of such monomolecular layer may be anywhere from 20 to 100 Angstrom, depending on the particular biological particle forming such layer.

The monomolecular layer coated substrate is next exposed to a second solution, or sample thereof, suspected of containing the second immunologically reactive biological particles that are specific to the first biological particles in a direct test for such second particles. This exposure is generally accomplished by immersing the monomolecular layer coated substrate in the second solution for a time interval which is again an inverse function of the concentration of the second biological particles in the second solution. Since the concentration of the second particles in the second solution is generally much less than the concentration of first particles in the first solution, the immersion step generally takes much longer than the time interval for forming the first biological particle monomolecular layer 11, and may take up to 24 hours. Presence of the second biological particles in the second (test or suspect) solution results in the formation of a second substantially complete monomolecular layer 12 on the substrate as depicted in FIGS. 3a and 3b as a result of the second biological particles immunologically reacting with the first biological particles to become bound thereto. After the substrate has been sufficiently exposed to the second solution, the coated substrate is removed therefrom and is rinsed with a suitable solution which, in many cases, may be tap water, distilled water or a salt solution thereof depending upon the solution in which the second biological particles were contained. This rinsing step is again utilized to prevent an excess buildup of the second biological particles on the substrate as well as to minimize nonspecific absorption due to the second solution often containing a great number of other type biological particles such as in a sample of human serum. The coated substrate is then dried in a manner described hereinabove, if the following step of forming an opaque, porous, nonreactive layer on the substrate requires a spraying process, otherwise the drying is not required. Absence of the second biological particles in the second solution results in no formation of the second monomolecular layer on the substrate.

A layer 13 of third particles characterized as being nonreactive with substrate 10 and the biological particles forming monolayers 11 and 12 is next formed over the entire coated surface of the substrate to form the third and outermost layer as depicted in FIGS. 4a and 4b. In the case where the second solution did not contain the second biological particles, layer 13 forms only a second layer on substrate 10 as shown in FIGS. 6a and 6b. Nonreactive layer 13 must be sufficiently porous so that a subsequent exposure of the coated substrate to a cleaving agent solution permits the cleaving agent to seep through layer 13 as will be described hereinafter. Because of the subsequent cleaving agent solution exposure, the material of layer 13 must also be nonreactive with the cleaving agent. Finally, porous, nonreactive, layer 13 must be opaque so that it is visible to the unaided eye whereas monomolecular layers 11 and 12 are normally not visible. The opaqueness is obtained by having layer 13 be substantially thicker than monolayers 11 and 12 and is also determined by the material forming such layer. Opaque layer 13 may be formed of virtually any material that exists in discrete small particle form, or that forms a porous continuous layer, that will adhere to the biological particle layer (and substrate 10 surface in the second embodiment) and has the aforementioned characteristic of being nonreactive with the first and second biological particles, substrate and cleaving agent solution. Thus, layer 13 may be formed of metal particles such as nickel or gold, and in such case the layer 13 is formed by dipping the coated substrate into an agitated third solution containing a relatively high concentration of such nonreactive particles so as to form a layer of the particles which are in contact with each other or in slightly spaced apart relationship. Glass or plastic particles in a suitable agitated solution may also be utilized to obtain layer 13. The solution in which the metal, glass or plastic particles are contained may simply be water. In the case wherein the coated substrate is dipped into a solution of the small particles, there is no need to dry the coated substrate after the monomolecular layer 12 coated substrate has been rinsed since the solution containing the particles will moisten the coated substrate. The size of the generally spherical particles, whether they be of metal, glass or plastic, can be over a wide range of values (diameters of 0.1 to 100 micrometers) since the function of layer 13 is merely to present a porous layer to the cleaving agent solution to be utilized hereinafter, as well as to be opaque so that layer 13 is clearly visible to the unaided eye when viewing the light reflected off the coated surface of substrate 10, or viewing the transmitted light if the substrate is transparent.

An alternative method for forming layer 13 on the substrate is to utilize the conventional aerosol spray can filled with virtually any material that again is nonreactive with the substrate, biological particles and cleaving agent, is porous and forms an opaque layer. The coated substrate should be in a dry condition prior to this spraying process in order to obtain more efficient sticking of layer 13 to layer 12 (or 11). The aerosol is a suspension of fine solid or liquid particles in a gas so that layer 13 may be comprised of solid or liquid particles. As typical examples, a light spray of the dried, coated surface of the substrate with MS-122 FLUOROCARBON, a release agent dry lubricant product of Miller-Stephenson Chemical Company and which consists of an aerosol preparation of a low molecular weight synthetic resin polymer wax sticks to the outer surface of the biological particle layer and has a white appearance. As another example of the wide range of sprayable materials which can be used to form layer 13, a light spray of SURE a trademarked men's deodorant product of Proctor and Gamble Company has been found to be satisfactory. Thus, it can be seen that virtually any sprayable material that will stick to the outer biological particle layer, is nonreactive therewith and with the subsequent cleaving agent solution, is porous and opaque, is suitable for the purposes of forming layer 13. The thickness of the sprayed-on layer 13 is substantially greater than the thickness of monomolecular layers 11 and 12, and is typically in the range of 1 to 10 micrometers, but can be in a range as great as 0.1 to 100 micrometers. The ranges for the discrete particle sizes or sprayed-on layer thicknesses may be different for different materials due to the different porosity and opaqueness thereof.

After the nonreactive, porous, opaque layer 13 has been formed over substantially the entire outermost coated surface of substrate 10, a portion of the layer 13 coated surface of substrate 10 is exposed to a cleaving agent solution such as a weak acid solution, alkaline solution, or high salt concentration solution, in this first embodiment of my invention wherein one (or more) drops of cleaving agent solution is deposited generally at the central region of the coated substrate surface. Since opaque layer 13 is nonreactive with the cleaving agent and porous thereto, the cleaving agent solution seeps through layer 13 in the region of deposition and, in the presence of the monomolecular layer 12 of second biological particles this cleaving agent solution cleaves the bond between the first and second biological particles in such region so that a corresponding portion of monomolecular layer 12 is removed along with the corresponding portion of layer 13 attached thereto as depicted in FIGS. 5a and 5b wherein only the monomolecular layer 11 of first biological particles remains on substrate 10 in the region where the cleaving agent solution was applied. Since layer 13 is opaque and therefore clearly visible to the unaided eye, there is a significant contrast when viewing the light reflected off or transmitted through (in the case of a transparent substrate) layer 13 between the portions of the coated substrate where layer 13 remains and the central region where it has been removed due to the cleavage of the bond between the first and second biological particles. This clearly visible contrast between the portions of the coated substrate exposed and not exposed to the cleaving agent solution is thus indicative of the presence of the second biological particles in the solution suspected of containing them, and is also indicative of the resultant immunologic reaction between the first and second biological particles. In the case wherein the second solution does not contain the second biological particles, application of the cleaving agent solution to region 14 as indicated in FIG. 6a has no reaction on the coated surface of the substrate since there is no bond between biological particles to be cleaved, and opaque layer 13 remain complete. In the case of the cleaving agent being an acid solution, the acid solution utilized is generally a weak one, that is, it is sufficiently strong to cleave the bond between the layers of first and second biological particles, but is not sufficiently strong to cleave or otherwise affect the bond between the first layer 11 of biological particles and solid surface of substrate 10 to which it is adsorbed. A 0.1 normal (N) citric acid solution is suitable for the purposes herein described. The range of concentrations of the citric acid for obtaining the desired results are approximately 0.01 to 1.0 N. Other suitable weak acids that may be utilized are 0.1 N malic acid and 0.1 N formic acid. Stronger acids such as hydrochloric acid and sulfuric acid may also be utilized, but in a much smaller concentration (i.e., approximately 0.01 N). The weak acid solution that may be utilized in my invention may be generally described as being any acid solution that does not attack the substrate or third layer material and has a pH in a range between 2 and 5 although a pH as low as 1.0 was found to be satisfactory (using 0.1N hydrochloric acid). As noted hereinabove, alkaline and high salt concentration solutions may also be used as cleaving agents. The alkaline solution useful herein has a pH in the range 9–13, and typically, a 0.2 N sodium hydroxide solution has been used to cleave the bond between egg albumin and its antigen. Various salt solutions, such as Na Cl and NaI are known to function as cleaving agents. Thus, a 1.79 molar Na Cl solution cleaves pneumoccal polysaccharide and its antibody. The comparison between FIGS. 5a and 6a, as well as between FIGS. 5b and 6b thus indicates the cases wherein the second biological particles are present, and are not present, respectively, in the second solution suspected of containing such particles.

A second, and preferred embodiment of my invention is illustrated in FIGS. 7a–11b and will now be described. The major distinction between this second embodiment, as well as the third embodiment described with reference to FIGS. 12a–14b as compared to the first embodiment described hereinabove is that the entire coated substrate is exposed to the cleaving agent solution in the second and third embodiments instead of merely having a small region thereof be exposed to the cleaving agent.

Referring now in particular to the second embodiment of my invention, and with specific reference to FIGS. 7a and 7b, after selection of substrate 10, a single (or more than one) drop of the first solution containing the first biological particles is deposited on the top major surface of substrate 10 and results in a monomolecular layer 11 having the pattern of the deposited drop being adsorbed onto the surface of the substrate. The first particle solution drop is preferably deposited approximately in the middle of substrate 10 merely as a convenience. Due to the fact that only a single drop of the first solution may be utilized, and depending on the humidity in the room, the substrate may be stored in a moist chamber to prevent too rapid an evaporation of the solution containing the first biological particles, although this storage in a moist chamber is not always required. An advantage of this second embodiment of my invention is that the smaller area size of monomolecular layer 11 as compared to the layer covering the entire substrate surface in the first embodiment results in conserving the amount of biological material used in the process. After monomolecular layer 11 has been adsorbed on substrate 10, a rinsing of the coated surface of the substrate may be performed as in the case of the first embodiment.

The monomolecular layer coated substrate of FIGS. 7a and 7b is next immersed in the solution suspected of containing the second biological particles and, in the case wherein this second solution does contain such particles, such particles immunologically react with the first biological particles in monomolecular layer 11 to form a monomolecular layer 12 of the second biological particles having a pattern of the same shape as layer 11 as illustrated in FIGS. 8a and 8b as well as forming a monolayer 12a along the remaining surfaces of substrate 10 due to nonspecific sticking of other particles in the suspect solution. The time of immersion of the coated substrate in the second solution is determined as in the first embodiment, that is, in an inverse function of the concentration of the second biological particles in the second solution. The pattern of the first monomolecular layers 11 and 12 is generally a round spot as illustrated. After removal of the coated substrate from the second solution, the coated substrate is preferably again rinsed and may be dried, depending upon the manner of application of the subsequent opaque layer as described with reference to the first embodiment of my invention.

Figure 11B:
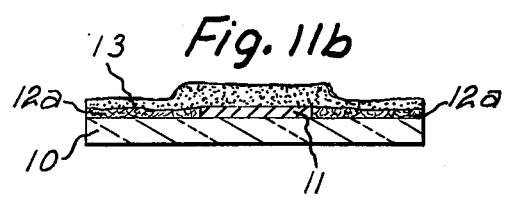
Figure 12B:
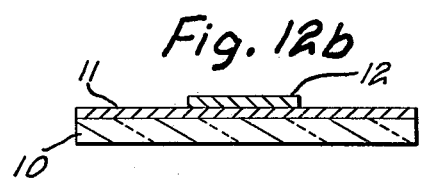

The nonreactive porous, opaque layer 13 is next formed on the coated surface of substrate 10 in the same manner as with respect to the first embodiment in that the material is applied over the entire top surface of substrate 10 so that it is in contact with the biological particle layer(s) 12 and 12a as illustrated in FIGS. 9 and 9b. After layer 13 has been formed on the substrate, by either spraying the suitable aerosol onto the coated surface of the substrate, or dipping the coated substrate into a solution containing small particles of the particular material forming layer 13, the entire coated substrate is then dipped momentarily into the cleaving agent solution for cleaving the bond between the layer of first and second biological particles, if the second layer 12 does, in fact, exist on the substrate. Since the biological particles exist only as a small area pattern on substrate 10, the coated substrate, after removal from the cleaving agent solution appears as in FIGS. 10a and 10b, assuming that the solution suspected of containing the second biological particles did contain them. Thus, the coated substrate appears to the unaided eye in FIG. 10a the same as in FIG. 5a in that the top surface of substrate 10 is covered with an opaque layer 13 with a significant contrast visible in the region 11 wherein the portion of the opaque layer 13 has been removed along with the entire second biological particle layer 12 (in the case of the second embodiment) by the cleaving agent solution. As in the case of FIGS. 6a and 6b in the first embodiment, if the second solution does not contain the second biological particles, the coated substrate after removal from the cleaving agent solution has a complete layer 13 of opaque material on substrate 10 as depicted in FIGS. 11a and 11b.

Referring now to FIGS. 12a–14b there are illustrated the different appearances of the coated substrate in a third embodiment of my invention. In this third embodiment, the substrate 10 is dipped into a first solution known to contain the first biological particles so that the entire top surface of substrate 10 has adsorbed thereon a monomolecular layer 11 of the first immunologically reactive biological particles as in FIGS. 2a and 2b in the first embodiment, and is then preferably rinsed. However, as distinguished from the first embodiment, only a small portion of the coated substrate is exposed to the second solution suspected of containing the second biological particles. This exposure to the second solution may be accomplished by depositing a single (or more than one) drop of the second solution approximately in the center of the coated substrate. Since the second solution is generally a dilute solution of the second biological particles, the coated substrate may be stored in a moist chamber as in the case of the second embodiment during formation of the second biological particle layer wherein the second biological particles immunologically combine with the first biological particles.

Figure 13A:
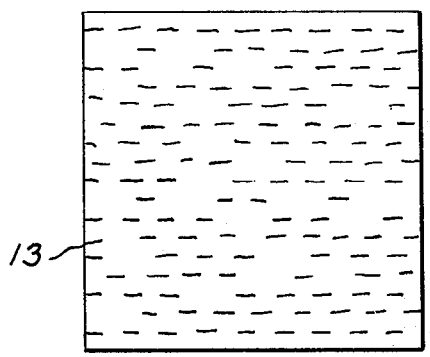
FIG. 13a is a plan view of the coated substrate of FIG. 12a after the nonreactive, opaque, porous third layer has been formed.
Figure 14A:
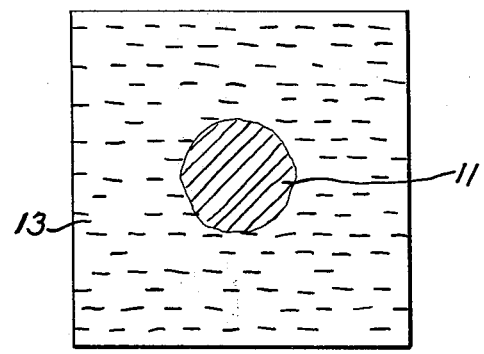
FIG. 14a is a plan view of the coated substrate of FIG. 13a after exposure to the weak acid solution.
Figure 13B:
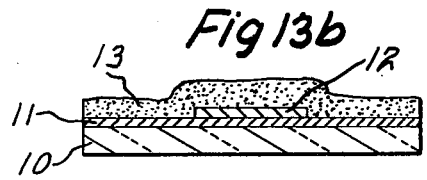
Figure 14B:
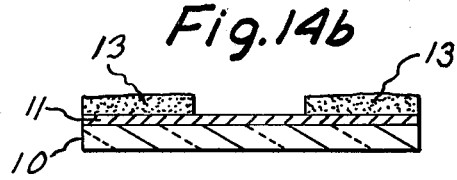

After the small, generally circular pattern layer 12 of second biological particles has been formed on the substrate, the coated substrate is removed from the moist chamber, rinsed, and may be dried as determined by the subsequent opaque layer application process as described hereinabove. The coated substrate, after the nonreactive, porous, opaque layer 13 is formed thereon, appears as illustrated in FIGS. 13a and 13b.

After layer 13 has been formed on the substrate, the coated substrate is dipped momentarily into the cleaving agent solution so that if the layer of second biological particles 12 exists on the substrate, the bond between the first and second biological particles is cleaved by the cleaving agent and the second biological particle layer 12 with the corresponding overlying attached portion of layer 13 is removed from the substrate. The coated substrate then has the appearance depicted in FIGS. 14a and 14b wherein all of the top surface of substrate 10 is covered by opaque layer 13 except for the small generally circular region located approximately in the middle of the substrate surface in which area exists only the first monomolecular layer 11 of first biological particles. As in the case of the FIGS.

5a, 5b and 10a, 10b embodiments, the contrast between the portion of the substrate surface where the bond between the first and second biological particles was cleaved and the remaining portion of the substrate is readily visible. In the case wherein the solution suspected of containing the second biological particles did not contain them, the coated substrate has the same appearance as depicted in FIGS. 6a and 6b, that is, the entire top surface of substrate 10 remains covered with nonreactive, porous, opaque layer 13.

The above descriptions of the three embodiments of my invention all relate to a direct test for the detection of the second biological particles as a result of an immunologic reaction occurring on the substrate surface. My method and apparatus utilizing the nonreactive, porous, opaque layer 13 can also be used in an indirect or inhibition test for the detection of particular immunologically reactive biological particles since the general purpose of my invention is to distinguish between a monomolecular layer of first biological particles and a bimolecular layer of first and second biological particles. The principal of the inhibition test is that antigen particles, if present in sufficient quantity, will neutralize free antibodies in solution. This reaction will prevent the antibodies from forming observable complexes (i.e., a bimolecular layer) when the substrate with an antigen monomolecular layer adsorbed thereon is exposed to the solution.

In the above three embodiments of a direct test for the existence of the second biological particles in the second solution, the first biological particles adsorbed onto the surface of substrate 10 are generally a particular antigen whereas the second biological particles are generally the antibody that is specific to that particular antigen. However, the first biological particles do not have to be the antigen, and can be the antibody so that the second biological particles would then be the antigen to which the antibody is specific.

The inhibition test is accomplished as follows. A monomolecular layer of first biological particles, assume them to be the antigen, is adsorbed on substrate 10 as in the direct test described hereinabove, along the entire top surface of substrate 10 or along only a small, generally circular portion thereof. The second solution is prepared by adding a sample to be tested to a solution of the specific antibody in a vial or other suitable container. The vial is then stored for a time interval sufficient for the antibody to complex with the antigen in the test sample, if the antigen is present therein. The vial is preferably agitated to increase the rate of complexing. Finally, the antigen monomolecular layer coated substrate is immersed in the second solution, and after a suitable period of time (again up to 24 hours), the substrate is removed, may be rinsed and dried, and the nonreactive, porous, opaque layer 13 is formed thereon and subsequently the coated substrate is exposed to the cleaving agent solution as described hereinabove. The results of the inhibition test are the opposite of the direct test, that is, presence of the antigen in the sample being tested produces no contrast in opaque layer 13, i.e., produces no second monomolecular (antibody) layer on the substrate, whereas removal of a portion of opaque layer 13 to produce the significant contrast readily visible to the unaided eye indicates absence of the antigen in the test sample. In like manner, the inhibition test for the detection of a specific antibody is performed similarly to the inhibition test for the antigen with the obvious substitution of antigen for antibody, and antibody for antigen in each of the steps.

In the description of my invention hereinabove, reference has been made to first and second immunologically reactive biological particles wherein the second biological particle is specific to the first. The use of this language is deliberate and the immunologically reactive antigen biological particles that may be utilized, and detected, with my invention are meant to include hormones, viruses, bacteria, enzymes and other particles which can be readily grown or otherwise isolated and collected or are present in human serum or other solution being tested. However, my invention is further useful with virtually any pair of biological particles that will react (combine) with each other. That is, rather than using the immunologically reactive antigen-antibody, my invention also includes other forms of biological interactions between large molecules based on non-immunological specificities, such as for example, the binding of enzymes to their biological substrates, or hemoglobin to haptoglobin.

An important application of my invention is in the case wherein the solution being tested has only a very small concentration of the suspect biological particles therein. In such case, my monomolecular layer coated substrate remains immersed in the second (test) solution for a sufficient interval so that the second (low concentration) biological particles form a monomolecular layer thereof, which layer does not require the many molecules, especially if the second embodiment of my invention (note especially FIGS. 8a and 8b) is utilized.

The second solution utilized in my invention is generally a human serum sample, although it can be other type solutions appropriate to the particular biological particle being investigated. In the direct test case wherein it is sought to detect an antibody, such as in the case of syphilis or gonorrhea, the antibody is detected in the human serum of a patient known or suspected to have the particular disease. Alternatively, in the inhibition test where one wants to detect an antigen such as hepatitis HAA, the antibody may be developed in a goat, rabbit or other suitable animal and the appropriate quantity of this animal serum is mixed with the human serum of a patient to be tested for hepatitis.

Several examples of my invention indicating various antigen-antibody pairs and nonreactive, porous, opaque layer 13 material that is suitable will now be described. In each of the examples, substrate 10 is fabricated of a solid material that is nonreactive with the biological particles and with the material forming opaque layer 13, a small glass or plastic slide 25 mm square and ¼ mm thick being suitable for my purposes. Also, in some of the examples the step of exposing the top substrate surface to a first solution containing the first immunologically reactive biological particles in order to adsorb a monomolecular layer thereof therealong will be described as depositing a drop thereof at the center of the top surface of the substrate as described with reference to the second embodiment of my invention relative to FIGS. 7a and 7b in order to conserve the first biological particles. However, it should be understood that the entire top surface of the substrate may have the first monomolecular layer adsorbed thereon (EXAMPLE 1) as described with reference to the first and third embodiments of my invention by dipping the entire substrate into the first solution, and this approach might find value in cases wherein drops of several solutions suspected of containing the second biological particles are deposited in spaced apart relationship along the monomolecular layer covered substrate in order to conduct several tests almost simultaneously. All of the steps in the various examples can be conducted at room temperature, that is, in a temperature range of approximately 65°–75°F which is not critical to my invention. Finally, it should be understood, as has been implied hereinabove, that the description of my substrate as being "nonreactive" with the biological particles and opaque layer applies to its chemical and biological inertness to the extent that it will not attack or destroy such biological particles or opaque layer. Thus, the substrate is reactive to the extent that it has a capability of having the first biological particles adsorb thereon as a monomolecular layer. In like manner, the material of opaque layer 13 is nonreactive with the biological particles (and substrate), but has the capability of binding or adhering to the layer of second biological particles (or layer of first particles in absence of the second layer).

The following examples, which are to be regarded as illustrative and not as limiting, show the use of the method and apparatus of my invention for detecting various specific biological particles, as described hereinabove.

EXAMPLE 1

BOVINE SERUM ALBUMIN DIRECT TEST

The source of the antigen is Pentex Bovine Albumin, Crystal, 10% solution, a product of Miles Laboratories. A 1% solution of the BSA antigen in physiological saline (0.154N) is prepared and ordinary microscope cover slides are immersed and incubated in the solution for about one minute. After removal of the BSA antigen monolayer coated slides from the solution, they are rinsed with distilled water and dried with compressed air. The source of the antibodies is also a commercial preparation from Miles Laboratories, "Pentex Rabbit Anti-Bovine Albumin Serum". Dilutions from 1:1 to about 1:10,000 by factors of 5 of the antiserum in physiological saline are prepared and drops of 1/20 milliliter size of these dilutants are applied onto the BSA covered slides and incubated for two minutes. The slides are then rinsed with distilled water and dried with compressed air. At this time the bimolecular Ag/Ab layers may be present on the glass slide surfaces but are not visible to the unaided eye. The Ag/Ab layer coated slides are then lightly sprayed (each for approximately 2 or 3 seconds) to provide a thin coating of a synthetic resin polymer wax (the MS-122 product described hereinabove) as an opaque film that sticks to the Ag/Ab layers and gives the slides a whitish appearance. Finally, the coated slides are immersed in a citric acid solution with a pH of 2.0 for 1 minute and then removed. The acid solution cleaves the bonds between the BSA antigen and antibodies. When the antibodies are removed by the cleaving action, some of the fluorocarbon particles are also removed. A clear spot on the slide, indicating removal of substantially all the fluorocarbon particles from such spot, indicates removal of a complete layer of the BSA antibodies, while a partially clear spot indicates that only an incomplete antibody layer had been formed. No change in appearance of the white coating on the slide indicates that no antibody layer was formed and therefore that the particular antiserum dilutant (or a solution suspected of containing the BSA antibodies) did not contain them in sufficient quantity to be detected. By this method BSA antibodies are detected in dilutions as low as 1:1000 from the rabbit anti-bovine albumin serum which corresponds to a concentration of the antibodies of approximately $10^{-6}$ grams per milliliter of serum. This sensitivity can be improved by increasing the two minute incubation time, by agitation of the antiserum solution, and by using a larger volume of serum. The use of the various dilutions of the antiserum thus results in an endpoint in a titration test, and allows quantitative determinations of the antibody concentration. By doing an inhibition test, titration of the antigen can also be carried out.

EXAMPLE 2

TOXOPLASMA DIRECT TEST

A derivative of purified toxoplasma is used as the antigen. The source of the antigen is a peritoneal extract from one adult mouse which had been innoculated three days prior to the sacrifice with a dilute innoculum (using 100 ml sterile saline) of Toxoplasma gondii, a protozoan parasite. The extract is then sonicated for about 20 minutes. The preparation is then clarified by centrifugation, and the supernatant is then applied to the surface of a glass slide as a discrete droplet of about ¼ inch diameter. The slide is then incubated in a moist chamber (an enclosure containing wet sponges) for about 30 minutes at room temperature. After removal of the Toxoplasma Ag layer coated slide from the moist chamber, the slide is rinsed with distilled water and blown dry. The slide is then placed in a small well in a plastic tray, and the well is filled with a 0.154N saline (physiological saline) solution of 1:10 dilution containing antibody to Toxoplasma. The antibody (derived from a goat) is a commercial preparation from Canalaco Diagnostics of Rockville, Md. The slide is immersed and incubated in the antibody solution for two hours at room temperature with the solution being agitated. The slide is then removed from the solution, rinsed with distilled water and blown dry. At this time the Ag/Ab layers are present on the slide surface but are not visible to the unaided eye. The Ag/Ab layer coated slide is then lightly sprayed (for approximately 2 or 3 seconds) to provide a thin coating of a synthetic resin polymer wax (the MS-122 product described hereinabove) as an opaque film. Finally, the coated slide is dipped into an acidic solution (0.2 molar sodium acetate buffer with pH = 3.6). This solution permeates the opaque film and cleaves the antigen-antibody bond. In the region of the cleaved antigen-antibody bond the opaque synthetic resin polymer wax is released from the slide and a hole appears in the opaque film which is readily visible to the unaided eye.

VERIFICATION TESTS OF EXAMPLE 2

To verify that the observed hole is due to the presence of a layer of the Toxoplasma antibody, a serum not containing such antibody is substituted in the above experiment for the antibody solution. After the acidic solution is applied, no visible hole in the opaque film results.

A second verification test utilizes a 0.154 molar sodium chloride solution as a substitute for the antibody solution. Such solution is known to be isotonic to blood plasma but does not contain antibodies to Toxoplasma. Again, no hole results in the opaque layer after exposure to the acidic solution.

EXAMPLE 3

HUMAN CHORIONIC GONADOTHROPHIN (HCG) TEST

The test is conducted as in EXAMPLE 2 above with the antigen solution being 2 mg HCG per ml distilled water and the antibody to HCG béing undiluted and obtained from a rabbit.

EXAMPLE 4

OPAQUE LAYER TEST

The above test utilizing a material other than the synthetic resin polymer wax spray also produces a hole in the opaque layer readily visible to the unaided eye in the presence of the second monolayer. The material is a solution of polystyrene (molecular weight = 33,000) in acetone. A drop of water is first deposited on the bimolecular coated substrate and then a drop of the polystyrene acetone solution is deposited on the water drop, mixes with it, and forms a white precipitate forming the opaque layer.

EXAMPLE 5

SUBSTRATE TEST

The above test is conducted on substrates such as a plastic laboratory dish, thin film of gold on glass slide and silicon dioxide film on silicon wafer and provides equally satisfactory results as for the glass slide substrate.

From the foregoing description, it can be appreciated that my invention makes available an improved method and apparatus for detecting immunological and other forms of biological reactions occurring at a solid surface by a direct visual observation with the unaided eye wherein the substrate employed may be virtually any solid material that is nonreactive with the biological particles and the nonreactive, porous, opaque layer employed as the outermost coating on the substrate. Due to its opaqueness, the outer layer is clearly visible to the unaided eye and the cleaving of the bond between first and second biological particles on the substrate surface is readily apparent by a concurrent removal of the portion of such opaque layer at the end of the testing procedure.

Having described three embodiments of my method and apparatus for detecting biological particles, and several examples of the method with specific antigen-antibody pairs, it should be obvious that modification and variation of my invention is possible in light of the above teachings. Thus, in the case of the biological pair being large molecules such as an enzyme and its biological substrate (the molecule with which it reacts, such as a protein or sugar) either of these molecules can comprise the first layer, and the other molecules the second layer. Also, the opaque layer 13 may be formed as a thin metal film, electroplated or evaporated onto the biological particle coated substrate, rather than using the metal particles in solution as described hereinabove. An advantage of this type layer is that the metal film (which may be of silver) can be significantly thinner than the size of particles used in the solution, a few Angstroms thick film being clearly visible. Finally, the final step in my method of detecting the biological reaction, i.e., the step of examining the opaque layer coated substrate after its exposure to the cleaving agent, is not limited to a visual observation with the unaided eye. Thus, in a commercial application of my invention, especially for large scale testing, optical instrumentation would often be utilized, a densitometer being a typical instrument for measuring the amount of light passing through the coated (transparent) substrate. My invention as described is now defined by the following claims.

What I claim as new and desire to secure by Letters Patent of the United States is:

1. A diagnostic method for detecting the presence or absence of select biological particles in a liquid sample comprising the steps of
    contacting surface area of a substrate with first biological particles, said first biological particles being specific to the select biological particles and being disposed as a first layer coating said surface area,
    contacting the coated surface area of said substrate with the liquid sample for a preselected period of time,
    depositing a porous, opaque layer of particles over said surface area so processed, said particles being nonreactive with the substrate member, the first biological particles, the sample liquid and the cleaving agent solution to be subsequently employed,
    contacting the surface area as modified by the preceding steps with a cleaving agent solution, said said solution being capable of selectively destroying such bonding as may exist between said first biological particles and select biological particles, and
    examining said porous, opaque layer to determine whether said porous, opaque layer is intact or has a portion thereof removed, the latter being indicative of the presence of select biological particles in the liquid sample.

2. The method set forth in claim 1 wherein
the examining step is accomplished with optical instrumentation.

3. The method set forth in claim 1 wherein
the step of contacting surface area of the substrate with first biological particles consists of dipping the substrate so as to form the monomolecular layer thereof along an entire major surface of the substrate member.

4. The method set forth in claim 1 wherein
the step of contacting surface area of the substrate with first biological particles consists of depositing at least one drop of a concentrated solution of the first biological particles on a small portion of a major surface of the substrate member.

5. The method set forth in claim 1 wherein
the step of contacting the coated surface area of the substrate with liquid sample is accomplished by immersing the substrate therein.

6. The method set forth in claim 1 wherein
the step of contacting the coated surface area of the substrate with liquid sample is accomplished by depositing at least one drop of the liquid sample on a small portion of the coated surface area.

7. The method set forth in claim 1 wherein
the step of depositing the porous, opaque layer consists of lightly spraying an aerosol of particles of inert material on the coated surface area so processed.

8. The method set forth in claim 1 wherein
the step of depositing the porous, opaque layer consists of applying a thin layer of metal particles thereon.

9. The method set forth in claim 1 wherein
the step of depositing the porous, opaque layer consists of depositing a thin layer of small glass particles on the surface area so processed.

10. The method set forth in claim 1 wherein
the step of depositing the porous, opaque layer consists of depositing a thin layer of small particles of a plastic material on the surface area so processed.

11. The method set forth in claim 1 wherein
the porous opaque layer is visible to the unaided eye.

12. The method set forth in claim 1 wherein
the step of contacting the surface area as modified with cleaving agent solution is accomplished by depositing at least one drop of a weak acid solution on a small portion of the porous, opaque layer.

13. The method set forth in claim 1 wherein
the step of contacting the surface area so modified with cleaving agent solution is accomplished by immersing the substrate in a weak acid solution.

14. The method set forth in claim 1 wherein
the cleaving agent solution is an acid solution having a pH in a range of 1 to 5.

15. The method set forth in claim 1 wherein
the cleaving agent solution is an alkaline solution having a pH in the range 9 to 13.

16. The method set forth in claim 1 wherein
the cleaving agent solution is a high salt concentration solution.

17. The method set forth in claim 1 wherein
the examining step is accomplished by viewing with transmitted light.

18. The method set forth in claim 1 wherein
the first biological particles are a particular antigen.

19. The method set forth in claim 1 wherein
the first biological particles are a biological substrate reactive with a particular enzyme which constitutes the select biological particles.

20. The method set forth in claim 1 wherein the examining step is accomplished by viewing with reflected light.

21. The method set forth in claim 1 and further comprising the step of
    rinsing the surface area of the substrate after the monomolecular layer of first biological particles has been adsorbed thereon.

22. The method set forth in claim 21 wherein
distilled water is used for the rinsing step.

23. The method set forth in claim 1 wherein
the first biological particles are a particular antibody.

24. The method set forth in claim 23 wherein
the select biological particles are an antigen to which the particular antibody is specific.

25. The method set forth in claim 1 wherein
the first biological particles are a particular enzyme.

26. The method set forth in claim 25 wherein
the select biological particles are a particular biological substrate reactive with the enzyme.

27. The method set forth in claim 1 and further comprising the step of
    rinsing the coated surface area after contact with the liquid sample.

28. The method set forth in claim 27 wherein
distilled water is used to rinse after contact with the liquid sample.

29. The method set forth in claim 27 and further comprising the step of
    drying the coated surface area after it has been contacted with the liquid sample and rinsed.

* * * * *